US009086495B2

(12) United States Patent
Radley et al.

(10) Patent No.: US 9,086,495 B2
(45) Date of Patent: Jul. 21, 2015

(54) OBJECT SCANNING PROTOCOL

(75) Inventors: Ian Radley, Bishop Auckland (GB); David Edward Joyce, Bearpark (GB); Martin Senior, Wetherby (GB)

(73) Assignee: Kromek Limited, Durham (GB)

( * ) Notice: Subject to any disclaimer, the term of this patent is extended or adjusted under 35 U.S.C. 154(b) by 1002 days.

(21) Appl. No.: 13/145,414

(22) PCT Filed: Jan. 21, 2010

(86) PCT No.: PCT/GB2010/050079
§ 371 (c)(1),
(2), (4) Date: Oct. 21, 2011

(87) PCT Pub. No.: WO2010/086636
PCT Pub. Date: Aug. 5, 2010

(65) Prior Publication Data
US 2012/0027175 A1 Feb. 2, 2012

(30) Foreign Application Priority Data

Jan. 27, 2009 (GB) .................................. 0901283.2
Jul. 17, 2009 (GB) .................................. 0912420.7

(51) Int. Cl.
*G01V 5/00* (2006.01)
*G01N 23/10* (2006.01)
*G01N 23/12* (2006.01)

(52) U.S. Cl.
CPC .............. *G01V 5/0016* (2013.01); *G01N 23/10* (2013.01); *G01N 23/12* (2013.01)

(58) Field of Classification Search
CPC ... G01V 5/0016; G01N 23/087; G01N 23/10; G01N 23/12; G06K 9/00577
USPC .............. 378/57, 58, 82–85, 86–89, 208, 210
See application file for complete search history.

(56) References Cited

U.S. PATENT DOCUMENTS 5,367,552 A    11/1994  Peschmann
2004/0017888 A1*  1/2004  Seppi et al. ..................... 378/57
(Continued)

FOREIGN PATENT DOCUMENTS

CN          201181282          1/2009
DE      10 2006 048 327        4/2008
(Continued)

OTHER PUBLICATIONS

International Search Report dated Oct. 13, 2010.
(Continued)

*Primary Examiner* — Toan Ton
*Assistant Examiner* — Mona M Sanei
(74) *Attorney, Agent, or Firm* — Drinker Biddle & Reath LLP

(57) ABSTRACT

A two step method of scanning objects to gain information about material content comprises the steps of providing a radiation source and a radiation detector system spaced therefrom to define a scanning zone therebetween. In a first scanning step, an object is moved relative to the source and detector system, intensity information about radiation incident at the detector system after interaction with the object as it passes through the scanning zone is collected, variation of intensity as the object moves through the scanning zone is used to identify anomalous structures and/or absence of homogeneity in the object. In a second, subsequent scanning step an object is located in fixed position in the scanning zone and collecting intensity information collected, analysed against a suitable functional relationship relating transmitted to incident intensity, and the results compared with a library of suitable data to provide an indication of material content.

29 Claims, 3 Drawing Sheets

(56) References Cited

U.S. PATENT DOCUMENTS

| | | | |
|---|---|---|---|
| 2004/0101097 A1 | 5/2004 | Wakayama | |
| 2006/0104414 A1 | 5/2006 | Mayo | |
| 2006/0227932 A1 | 10/2006 | Chapin et al. | |
| 2007/0147585 A1* | 6/2007 | Eilbert et al. | 378/57 |
| 2007/0280416 A1 | 12/2007 | Bendahan | |
| 2010/0208972 A1* | 8/2010 | Bouchard et al. | 382/132 |

FOREIGN PATENT DOCUMENTS

| | | |
|---|---|---|
| GB | 2 441 551 | 3/2008 |
| JP | 2005-321331 | 11/2005 |
| JP | 2006276011 A | 10/2006 |
| JP | 2007510922 A | 4/2007 |
| WO | WO 01/44791 | 6/2001 |
| WO | WO 2004/010127 | 1/2004 |
| WO | 2005045407 A1 | 5/2005 |
| WO | WO 2005/059594 | 6/2005 |
| WO | WO 2006/027756 | 3/2006 |
| WO | WO 2008/034232 | 3/2008 |
| WO | WO 2008/142446 | 11/2008 |
| WO | WO 2009/024818 | 2/2009 |
| WO | WO 2010/086636 | 8/2010 |

OTHER PUBLICATIONS

Written Opinion of the International Search Report.
JP Examination Report for JP Application No. 2011-546959, Nov. 26, 2013, 7 pages (including translation).
Xp-002601990—C.J. De Ruiter, O.M.E.J. Lemmens: In: "Proceedings of the NATO Advanced Research Workshop on Detection of Liquid Explosives and Flammable Agents in Connection with Terrorism, St. Petersburg, Russia, Oct. 17-19, 2007"; 2008, Springer, Dordrecht, The Netherlands pp. 211-212, pp. 3.

* cited by examiner

OBJECT SCANNING PROTOCOL

FIELD OF THE INVENTION

This invention relates to a protocol for scanning objects to gain information about content and to an apparatus for implementation of such a scanning protocol. The invention in particular relates to the scanning of objects such as containers expected to have relatively homogenous structure or contents, to identify both conformal anomalies in the object or container and constituent anomalies in the contents. The invention in particular relates to objects comprising containers of contained materials which by their nature will be expected to have a single generally homogeneous composition, for example fluid compositions such as liquids, including mixtures, solutions, emulsions, suspensions etc, like flowable compositions such as gels, pastes, creams, fine powders, and the like, aerosols etc. Where reference is made herein by example to contained liquids in objects such as liquid containers it should be appreciated that the invention is equally applicable to all such liquid, partly-liquid and other flowable materials having this essential mixed and generally homogeneous character when contained.

BACKGROUND

It is desirable to scan the contents of objects such as, for example bottles or other containers, at security and customs checkpoints to gain information about content based on radiation received at a detector after interaction with the object and obtain an indication that the contents of the object do not constitute a threat to security or a breach of customs regulations. It is also desirable to scan the contents of objects for other purposes such as quality control, content verification, degradation monitoring etc.

To ensure that the contents of an object are consistent throughout the object, or that an object does not contain hidden compartments, or components, or to ensure that the contents are what they are claimed to be, it may be useful to scan the object and contents so that a high energy ionising radiation beam traverses a cross section of the object. It can be possible to obtain an indication of the materials composition from a numerical analysis of the resultant transmitted radiation beam intensity data.

A preferred means of scanning the contents of an object is to cause the object to move relative to the high energy radiation beam and detector. For scanning relatively small objects, such as bottles that might be carried through an airport security checkpoint, for ease of operation it is desirable to move the bottle rather than the bulky and heavy radiation source and detector assembly. In either case, a relative linear movement of object through scanning zone effects a scan along a selected path through the object, for example under the action of suitable drive means.

It has been found that when the transmitted beam of high-energy ionising radiation is detected at a suitable detector after it has passed through the object and its contents, during a scan along a selected cross section of the object, the electric motor typically used to power a drive means driving the movement of the object relative to the radiation source and detector may cause electromagnetic signals that may interfere with the signal representative of the radiation detected at the detector, making it more difficult to analyse the signals to accurately identify the materials present in the object. There is also a compromise to be considered between the desire for fast throughput of objects (which tends to favour a high scanning rate) and the requirement, for effective materials identification, of a sufficiently high count rate through a given object feature. For both these and for other reasons the effectiveness of materials identification by numerical analysis of the transmitted radiation beam intensity might be diminished.

There is a need for an improved method, system and apparatus for undertaking scanning of objects and/or their contents using high energy ionising radiation, where a transmission radiation beam is measured by a detector and the radiation beam source and detector move relative to the object such that a cross section of the object can be scanned. There is a particular need for security applications for a high throughput rate method of scanning objects comprising containers of contained materials which by their nature will be expected to have a single generally homogeneous composition.

SUMMARY OF THE INVENTION

In accordance with the invention in a first aspect a method of scanning objects to gain information about content comprises the steps of:

providing a radiation source and a radiation detector system spaced therefrom to define a scanning zone therebetween;
in a first scanning step:
causing an object to move relative to the source and detector system and collecting intensity information about radiation incident at the detector system after interaction with the object and its contents as it passes through the scanning zone;
monitoring of variation of incident intensity as the object moves through the scanning zone;
using such variation of intensity to identify anomalous structures and/or absence of homogeneity in the object; and
in a second, subsequent scanning step:
locating the object in fixed position in the scanning zone and collecting intensity information about radiation incident at the detector system after interaction with the object as it is retained in fixed position in the scanning zone;
analysing the incident intensity data against a suitable functional relationship relating transmitted to incident intensity;
comparing the results of that analysis with a library of suitable data to provide an indication of material content.

Thus, in accordance with the general principles of the invention, an object under test is scanned by subjecting it to a source of incident radiation, and by detecting radiation at a detector system after interaction with the object and its contents, and in a particular preferred case at least by detecting radiation transmitted through the object and its contents. As will be familiar, the attenuation of radiation as it interacts with and for example as it is transmitted through an object can give useful information both about the structure of the object and about its composition and thus in the present case about the structure of the object and the composition of its contents. The method thus conveniently comprises determining the attenuation of incident radiation by an object in the scanning zone during each scanning step.

The invention is distinctly characterised in that the scanning operation comprises a multi-stage process, in particular in that it comprises at least two scanning steps. In a first scanning step, an object is caused to move relative to the source and detector system through a scanning zone, for example in that the object is moved relative to a static source/detector combination or in that a source/detector combination is moved about a static object. As a result it is scanned in a plurality of positions, as the object moves through the scanning zone in generally familiar manner. In a second, subsequent separate scanning step, the object is subject to a fixed scan. An object may be subject to multiple moving and/or fixed scans. Additionally, as described below, a machine cycle may be performed, for example before a scanning process or periodically during the scanning of multiple objects, comprising a calibration step in which an object is absent and intensity information about radiation incident at the detector system is used to generate reference data comprising incident radiation intensity for subsequent comparison with transmitted data to determine the attenuation thereof after interaction with the object in the scanning zone.

The method of the invention is particularly intended to be applied to objects which are by their nature expected to have essentially consistent composition and structure, for example comprising containers of contained materials which by their nature will be expected to have a single generally homogeneous composition, Examples of such contained materials include for example fluid compositions such as liquids, including mixtures, solutions, emulsions, suspensions etc, like flowable compositions such as gels, pastes, creams, fine powders, and the like, aerosols etc. These have been the subject of considerable security concern in recent years, for example in relation to airline security, contraband detection etc.

There are two areas of particular concern in scanning such objects. First, anomalous container structures or material inhomogeneity in the contents is in itself likely to be inherently suspicious. Second, there is a desire also to identify the composition of the contents specifically. The method of the invention essentially performs a two stage scan in which each area of concern is addressed efficiently. It is the intention of the method of the invention that information is obtained both about the internal structure of the object, for example to identify anomalies, and about its specific composition in an efficient manner.

The first, moving scan is used to identify anomalous structures, absence of homogeneity in the contents etc. It may for example additionally be used to provide a coarse level identification of the contents, but this is not a necessary feature of the invention. The second, static scan focuses on a single area of the object and obtains the count rate necessary to obtain a determination of, or more accurate determination of, composition of the contents. This static scan may focus on areas of interest identified by the first scan for optimum determination of composition or content.

The invention represents an improvement on mobile scanners which perform a line scan as an object is driven on a linear path via a suitable electrical conveyance means through the scanning zone, which can interfere with more accurate determination of the attenuation of the transmitted signal. The secondary scan is performed statically and therefore without such conveyance means being active, eliminating the interference, and providing a more sensitive secondary test. Additionally, the compromise between a higher screening rate for object throughput and a higher count rate for compositional analysis of suspicious material is resolved in a novel manner, in that a higher throughput rate may be maintained for the first, moving scan and a higher count rate obtained for the second, static scan which focuses on one or more single positions to collect data for a full compositional analysis.

In accordance with the invention, intensity information collected during the first scanning step is used to identify conformational anomalies and/or lack of homogeneity in the object and/or the contents thereof. In the preferred case, a numerical analysis of intensity information collected during the first scanning step will be made for this purpose.

The invention is particularly to be applied where the expectation is that an object under test should exhibit a relatively consistent response as it passes through the scanning zone, for example being a container of a generally constant wall thickness with contents of homogenous material. The only expected variation as such a container passes through the scanning zone should be gradual reflecting variation in through path length with variation in shape. For much of the container's path, the signal may be expected to be constant. Sudden discontinuities in attenuation of the signal are likely to indicate anomalous structure within the container, or multiple contents, either of which might be cause for suspicion.

Accordingly, the numerical analysis of intensity information collected during the first scanning step may conveniently take the form of a monitoring of variation of attenuation of incident intensity within predetermined tolerance limits as the object moves through the scanning zone. This may require suitable correction for other relevant known parameters, such as thickness/path length variation attributable to object shape. In particular, sudden discontinuities in the variation of attenuation of incident intensity which exceed predetermined tolerance limits, and especially sudden discontinuities in the variation of attenuation of incident intensity that do not correspond to thickness/path length variation attributable to object shape, will be interpreted as a result indicating conformational anomaly and/or lack of homogeneity in the object and/or the contents thereof.

In a normal security protocol making use of the invention, an object returning such a result will be classified as suspicious, and for example rejected by the scanning process and passed for further investigation.

The invention in particular comprises the collection and analysis of radiation after transmission through an object and contents under test. The invention in particular comprises a determination of the attenuation of that radiation relative to initial incident intensity. It is well known that the attenuation of transmitted radiation by a material is a specific material property which can be characteristically linked to and functionally related to certain physical parameters of the source radiation, such as incident intensity, incident energy etc.

This is used in the second stage of the invention in particular. In accordance with the method of the invention, intensity data comprising at least the intensity information collected during the second subsequent scanning step is numerically analysed against a suitable functional relationship relating transmitted to incident intensity and the results compared with a library of suitable data with the objective of providing an indication of material content. For example, a ratio is determined of incident and transmitted intensity, and this ratio is used, by fitting to a suitable analytical relationship for a suitable transmitted intensity attenuation mechanism, to determine a characteristic material data coefficient associated with the intensity attenuation mechanism. In the preferred case a determination is derived of a coefficient of mass attenuation by application of a suitable relationship such as the exponential attenuation law (Beer-Lambert Law). This can then be related to a library of equivalent coefficient data for expected target or component materials to gain information about the likely composition of the object and contents under scan.

In one example, a library may comprise a database of undesirable, threat or contraband materials that it is intended to screen for. A match to any item in the database will be returned as a result indicating presence of the material. In a normal security protocol making use of the invention, an object returning such a result will be classified as suspicious, and for example rejected by the scanning process and passed for further investigation. Conversely, in the absence of any such match an object will be classified as cleared by the scanning process.

Conveniently, initial intensity is measured via a calibration step in which the system is operated without an object in the scanning zone and intensity information about radiation incident at the detector system is used to generate an incident intensity dataset for the above analysis.

Optionally, the principles of materials identification described above in relation to the second subsequent scanning step may also be employed to perform a numerical analysis of the transmitted intensity information from the first scanning step, at least to perform a first, coarse level indication of material content. Optionally, transmitted intensity information from the first scanning step may be further processed and used to identify an optimum site for the collection of date for the second scanning step, for example being a site where a static count rate will be optimised. However, at least the principal purpose of the first scanning step is to identify anomalous structures and/or absence of homogeneity in the object by means of the simpler analysis set out above.

In a specific mode of operation the invention comprises the initial step of moving an object relative to the radiation beam from the source and the detector system so that the beam passes through the object and traces a path along a cross section of the object for a first scan which is for example a linear scan of transmitted intensity. The transmitted beam intensity is detected by a detector and the signals from the detector representing the radiation intensity incident on the detector are analysed for example to identify any unexpected variation indicating inhomogeneity and/or compared against a database library of equivalent theoretical, empirical or experimentally derived signals representative of suitable materials of interest and a determination is made of the closest match to the sample of interest. As the signal during the first, moving scan is made up of a number of data points each comprised of a relatively small number of detector counts that are distorted by the presence of electromagnetic interference from the motor that is driving the relative movement of the object, the detected signal is not always clean enough for accurate identification of the material contents of the object. However, the scan along a cross section through the object can show at least whether the material in the object is the same along the cross sectional path followed by the radiation beam.

If the material in the object appears to be the same along the cross section examined then, following completion of the first, moving scan, the motor is used to drive the object to a selected position where the radiation beam passes through the object and contents. This position may be selected from an analysis of the results of the first scan or otherwise. The motor is then switched off to prevent any electromagnetic interference and the radiation beam is passed through the object and contents to the detector where it is analysed without the interference from the motor to give a more accurate materials identification during a static scan cycle. The detector signal is analysed to derive a numerical material characteristic such as a coefficient of mass attenuation as a function of radiation energy and compared against a library of materials data to accurately identify the material or combination of materials present and/or to rule out the presence of any particular material contained within the library. Once the data has been collected from the detector the power can be restored to the motor for the object to be moved to the finishing point. Alternatively, the object can be moved to another static scan position and the power turned off from the motor to allow further data to be recorded.

If the analysis of the first, moving scan reveals some feature of interest in the object, for example a region with different content in a container such as a bottle where the contents should be consistent throughout the container, then the container may be further processed according to the security protocol being applied. The bottle may be rejected for physical analysis. Alternatively, the feature of interest may be subject to a static scan as above. Following the completion of the first scan, the motor will drive the object back to a position where the radiation beam will pass through the area of interest. The motor is then switched off to prevent any electromagnetic interference and the beam is passed through the object and its contents at the selected position during a single or multiple static scan cycles. The transmitted beam is detected and the detector output analysed as above.

Further positions of interest in a single object identified during the first scan can be tested if the first scan reveals a number of irregularities or areas of interest for further investigation.

Following the first scan structural properties of the contents of the object can be determined to define the location or locations for the static scan. An approximate identification of the material contents of the object might also be possible and such information can be used to select energy-selective absorbers and/or filters that can be entered into the beam path if appropriate to enhance the identification of certain materials and mixtures of materials.

The object being scanned can be positioned for movement in the vertical or horizontal plane depending on the application. For security or customs screening of liquids in bottles it is envisaged that the bottle will be mounted in a holder and moved through a generally vertical plane as mounting the bottle horizontally could result in spillage of threat materials. Mounting an object such as a bottle for vertical movement would require some sort of fastening to keep the object in place during the scanning movement so the object is preferably mounted at an angle of between 1° and 80° from vertical, preferably at an angle of between 5° and 45° and more preferably between 5° and 30°.

Many objects, such as containers, and for example bottles or cartons of liquids, have a regular shape defining a through thickness direction through which they might usually be scanned. For example such a thickness might be defined by the parallel sides of an object, or by diametrically opposite points on the surface of an object. The radiation beam can be arranged so that it is incident perpendicular to the surface of such an object. That is to say, it passes through an object normally to its surface and in such a through thickness direction. If the radiation beam is arranged to pass through the object at an angle other than perpendicular then the beam passes through an increased thickness of the object contents which can improve beam absorption and hence analysis of the object contents. For example, the radiation beam is preferably arranged to pass through an object at an angle of between 1° and 80° away from normal to the surface, preferably between 5° and 45° and more preferably between 5° and 30°, If the object is mounted at an angle of between 1° and 80°, preferably between 5° and 45° and more preferably between 5° and 30° such as is described above, then using a generally horizontal beam arrangement will give the desired increase in beam path length through the object contents.

Movement of an object during the moving scan, and in particular where applicable of an object holder, is carried out by a suitable conveying means, in particular adapted for linear movement through a scanning zone defined by the source and detector. For simplicity, the movement of the object holder or other conveying means may be carried out by an electrically powered rotary motor means connected by suitable gearing/ transmission to convert the rotational motion of the motor into a linear motion of the object being scanned. This could be through a belt or chain linkage between a pulley on the motor shaft and a pulley or other suitable means on a slide shaft that translates the rotational action at the pulley into a linear movement of the object holder and allows the object holder to move in either direction depending on the direction of rotation of the motor. Alternatively the motor can be arranged to rotate in only one direction and the change in direction of the linear slide shaft can be the result of a change of setting from one direction to the other of, for example a gearbox positioned between the motor and the slider shaft.

The radiation source preferably comprises a source to deliver high-energy radiation such as ionising radiation, for example high-energy electromagnetic radiation such as x-rays and/or gamma rays, and the detection system is adapted correspondingly to detect radiation in this spectrum. The radiation source for example is a broadband source such as a broadband x-ray or gamma-ray source capable of producing broad spectrum emission over a wide range of energies.

The method of the invention preferably comprises, at least in relation to the collection of intensity information during the second, static scanning step, and optionally also in relation to the collection of intensity information during the first, moving scanning step, the further step of resolving intensity information to be detected at a plurality of differentiated energy bands across at least part of, and preferably a major part of, the spectrum of the source. Intensity information is resolved into a plurality of differentiated energy bands in the sense that it is differentiated simultaneously into plural separate energy bands across the spectrum of the source. Advantageously, the step is performed prior to the step of analysing the incident intensity data against a suitable functional relationship relating transmitted to incident intensity, allowing this analysis to be performed on spectroscopically resolved data.

The detector system is preferably capable of detecting and collecting spectroscopically resolvable information about incident radiation in the sense that it is adapted to differentiate incident radiation simultaneously into plural separate energy bands across the spectrum of the source. The detector system preferably exhibits a spectroscopically variable response across at least a part of the source spectrum allowing such simultaneous differentiation of incident radiation into plural energy bands and thus allowing spectroscopic information to be retrieved and intensity information to be detected at a plurality of differentiated energy bands across the spectrum of the source.

This is particularly desirable in relation to the materials analysis step of the static scan. It is known that the attenuation of transmitted radiation by photoelectric absorption and other interactions is a characteristic material property that can vary characteristically with energy. Resolving the intensity information spectroscopically enables this to be exploited in the numerical analysis step whereat incident intensity data is processed against a suitable functional relationship relating transmitted to incident intensity to obtain a characteristic material property data item such as a mass attenuation coefficient. This improves the discrimination of match with the library of data.

For each "scanning event" (that is, for a measurement of intensity via a given radiation path incident upon and for example passing through the object and contents in a given position) an "intensity dataset" is collected representing the collected intensity incident at the detector system across at least part of a source energy spectrum. Preferably, in accordance with the method of the invention, each such intensity dataset is resolved across at least two and more preferably at least three separate energy bands across the spectrum of the source. An intensity dataset thus constitutes a dataset of intensity information related to frequency/energy which is resolvable into such a plurality of bands to produce a corresponding plurality of transmitted intensity data measurements relating to a given scanning event and hence a given transmission path through the object and contents under test.

In one possible embodiment, a single broad spectrum source may be used. In this embodiment the method of the invention may involve using a broad spectrum detector or detector array and/or a single narrow spectrum detector to detect incident radiation monochromatically. Alternatively incident radiation may be resolved spectroscopically with a single broad spectrum source incident upon a detector or detector array adapted to resolve information across the spectrum of source using the inherent properties of the detector and/or incident upon multiple detector arrays with narrow band responses. In the preferred case, incident radiation is resolved spectroscopically across at least three and more preferably at least five energy bands within the source spectrum. This can produce data susceptible of more powerful manipulation than monochromatic data. Thus, in this preferred case, the detector system is adapted to generate spectroscopic information about incident and especially transmitted radiation at least to the extent of resolving at least three and preferably at least five energy bands. Preferably, the detector exhibits a spectroscopically variable response across at least a substantial part of the spectrum of the radiation source allowing detailed spectroscopic information to be retrieved.

Similarly the source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

The source is preferably capable of generating a sufficiently broad spectrum of radiation to enable the spectral resolution necessary for the performance of the invention. Preferably the source generates radiation across at least one or more parts of the range of 20 keV to 1 MeV, and more preferably across at least a part, and for example a major part, of the range of 20 keV to 160 keV. For example the source generates radiation ranging across at least one bandwidth of at least 20 keV within the given range. For example the spectrum is such that at least three 10 keV bands can be resolved within that range.

It is preferable that the detector system is enabled to detect radiation in a manner which is spectroscopically resolvable by the data processing apparatus. Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the source spectrum. For example, the detector system or element comprises a semiconductor material or materials preferably formed as a bulk crystal, and for example as a bulk single crystal (where bulk crystal in this context indicates a thickness of at least 500 µm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_bTe$ where a and b are less than 1 and a and/or b may be zero.

Combination of these and any other such materials may be considered which give spectroscopic detection rather than merely detecting amplitude of radiation after interaction with object and contents.

Preferably, a beam of a particular geometry, such as a pencil beam geometry or a fan or curtain beam, is used aligned perpendicular to direction of movement of the object.

In a preferred embodiment a simple pencil beam may be provided in conjunction with a simple single pixel detector or linear array detector. Alternatively, a beam may be collimated to have a spread in at least one dimension, for example in conjunction with one or more linear detectors. Only one pixel is needed for the detector if a pencil beam geometry is used. A linear array or area array used with a pencil beam can provide the capability to detect additional information such a scatter radiation. If a fan beam geometry is used a linear detector is preferably arranged perpendicular to the direction of movement of the object and within the area of the beam. Conveniently, a linear detector may comprise a linear array of a plurality of individual detector elements.

The radiation source is adapted to emit such a beam. A collimator is preferably provided between the source and the object under test, for example in the vicinity of the source, to produce an emitted beam of suitable geometry from the source. In particular, the source beam is collimated to produce a pencil beam.

Additionally or alternatively, the beam may be collimated after interaction with object and contents under test, for example in the vicinity of the detector, to allow transmitted radiation to pass to the detector but for example to restrict any scatter radiation from reaching the detector.

At its simplest, the invention may simply comprise a method for extracting from intensity data, at single or multiple spectral bands, an indication of material composition in the transmission path, for example by calculating a mass attenuation coefficient for an object in the transmission path and making a suitable library comparison. It need not generate an image.

However, it is not excluded that the invention may form part of a scanning imaging system. In accordance with this possible embodiment, the dataset of information about radiation incident at the detector, or at a further, imaging detector, especially information collected during the first, moving scan, is used to generate an image of an object in the scanning zone.

Preferably the method comprises collecting data regarding the intensity of transmitted radiation after interaction with an object in the scanning zone and the data regarding the intensity of transmitted radiation is processed at the detector both numerically as above described and to produce one or more images and for example a succession of images as an object moves through the scanning zone.

For clarification it should be understood that where used herein a reference to the generation of image is a reference to the creation of an information dataset, for example in the form of a suitable stored and manipulatable data file, from which a visual representation of the underlying structure of the object under investigation could be produced, and references to displaying this image are references to presenting an image generated from such a dataset in a visually accessible form, for example on a suitable display means.

The method of the invention conveniently further provides the additional step of displaying such generated image or images, and in the case of multiple images might involve displaying such images simultaneously or sequentially.

Each collected image may be resolved spectroscopically across a plurality of bands each intended to generate an image across a part of the overall spectrum, so that the bands together allow the generation of an energy-differentiated composite image or succession of images.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
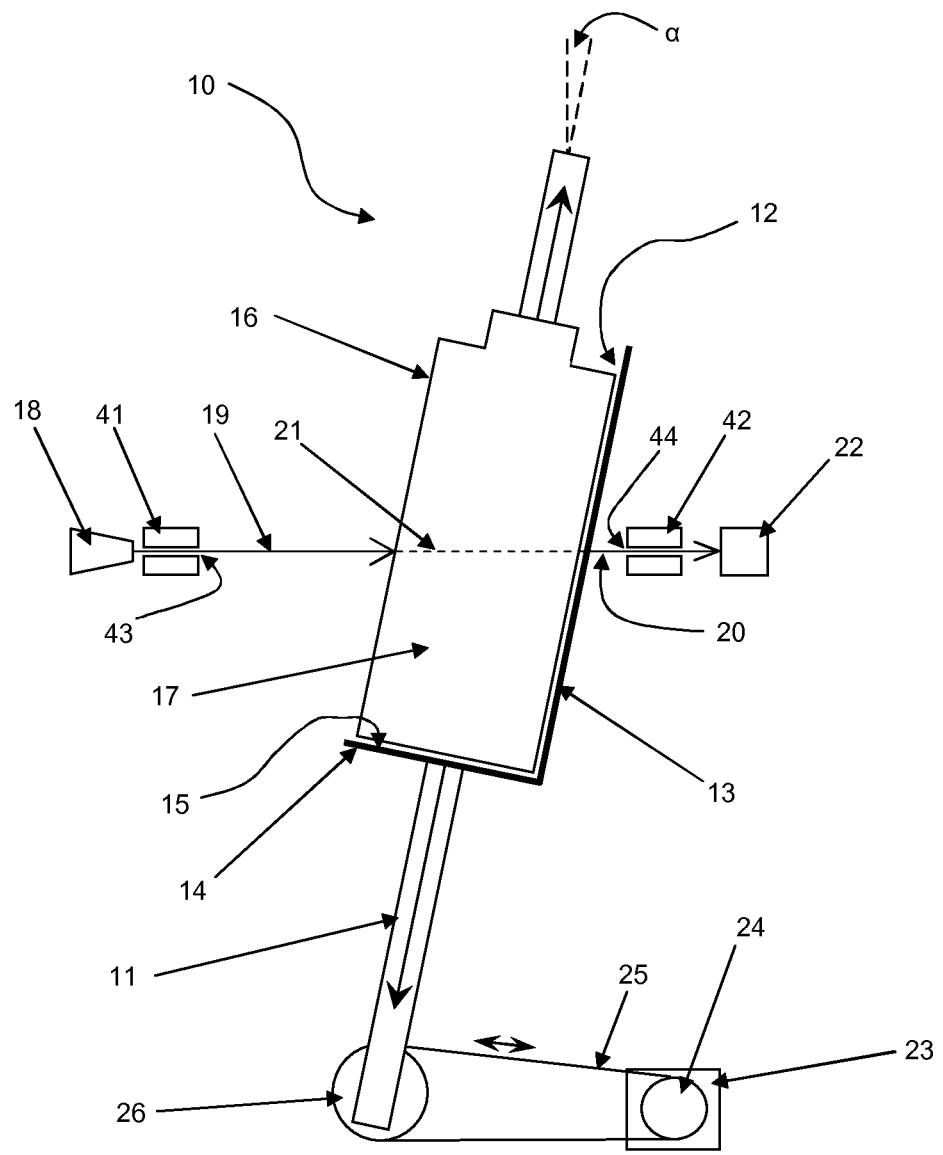
FIG. 1 is a schematic representation of an apparatus of the invention.

In the apparatus of the invention illustrated in FIG. 1 an embodiment of a possible apparatus to implement the invention is shown comprising a bottle scanner for scanning liquids in bottles and like objects using x-ray radiation.

The bottle scanner 10 is provided with a linear slider shaft 11 to move a bottle holder 12 that is fixedly connected to the linear slider shaft 11 for movement therewith. The linear slider shaft 11 is capable of moving the bottle holder 12 in two directions.

The bottle holder 12 comprises a back member 13 against which the bottle 16 rests and a base member 14 with a top surface 15 onto which the bottle 16 sits. The bottle 16 is nested against and into the bottle holder 12 by virtue of the holder and linear slider shaft being inclined at an angle $\alpha$. In the example this might be an angle of 15° from vertical. For a bottle, an angle of between 5° and 30° might be convenient. Other shapes of objects or containers might be held at different optimum angles.

The bottle holder back member 13 is preferably provided with an opening (not shown) to allow a clear path for the x-ray beam to pass from the bottle to the detector. The opening in the back member 13 could be a slot shaped aperture running from the top to the bottom of the back member. The slot aperture could be a narrow slot that provides some beam collimation with a width sufficient to allow the beam to pass through unimpeded but narrow enough to restrict any scatter radiation from reaching the detector 22. Additional or other alternative collimation of the beam on the transmission side could be provided.

The movement of the bottle holder 12 and bottle 16 along the linear slider shaft 11 is caused by the rotation of the electrically powered stepper motor 23. The motor causes the pulley 24 to rotate, which drives belt 25 which, in turn, drives the rotation of pulley 26. The rotational motion of pulley 26 is converted into a rotation of a suitable drive such as a screw drive (not shown) in the linear slider shaft 11 which creates the linear motion of the bottle holder 12. Other types of motor, such as electric servo motors, could be used.

The motor is capable of rotation in either direction and by controlling the direction of rotation of the motor the direction of movement of the bottle holder 12 and bottle 16 can be determined.

As the bottle is moved along the direction of the linear slider shaft it is caused to pass through an x-ray beam 19. The incident beam 19 is generated by a source 18, preferably a tungsten source so that it has a broad spectrum of energies present in the beam.

The x-ray beam 19 is aligned horizontally. As the bottle is inclined at an angle α from the vertical the beam does not strike the bottle perpendicular to the bottle's surface. This preferred arrangement gives an increased absorption path for the beam as it passes through the bottle and its contents.

The incident beam 19 passes through the bottle 16 and bottle contents 17 where absorption and scatter will take place along beam path 21 before the transmission beam 20 emerges from the bottle and is detected by detector 22.

The x-ray beam is preferably collimated by primary collimator 41 provided with aperture 43 and positioned close to the source 18 and is preferably a pencil beam with one dimensional geometry.

The transmission x-ray beam 20 is preferably collimated through an appropriate aperture 44 in secondary collimator 42 before it arrives at detector 22.

The detector 22 is preferably a single pixel aligned with the collimated x-ray beam. The detector generates a signal representative of the intensity and energy of interactions with photons from the transmission x-ray beam 20. These signals are then processed as detailed in FIG. 2 below. In the embodiment the detector comprises material capable of spectroscopic resolution of incident x-rays, and in the specific example comprises cadmium telluride (CdTe) although it will be appreciated that alternative materials could be used.

Additional analysis capability could be provided by the use of additional detectors to detect those parts of the x-ray beam that have been scattered in the forward and/or backwards directions. The transmission beam 20 and forward scattered x-ray beams could be detected by the use of linear or area arrays.

Figure 2:
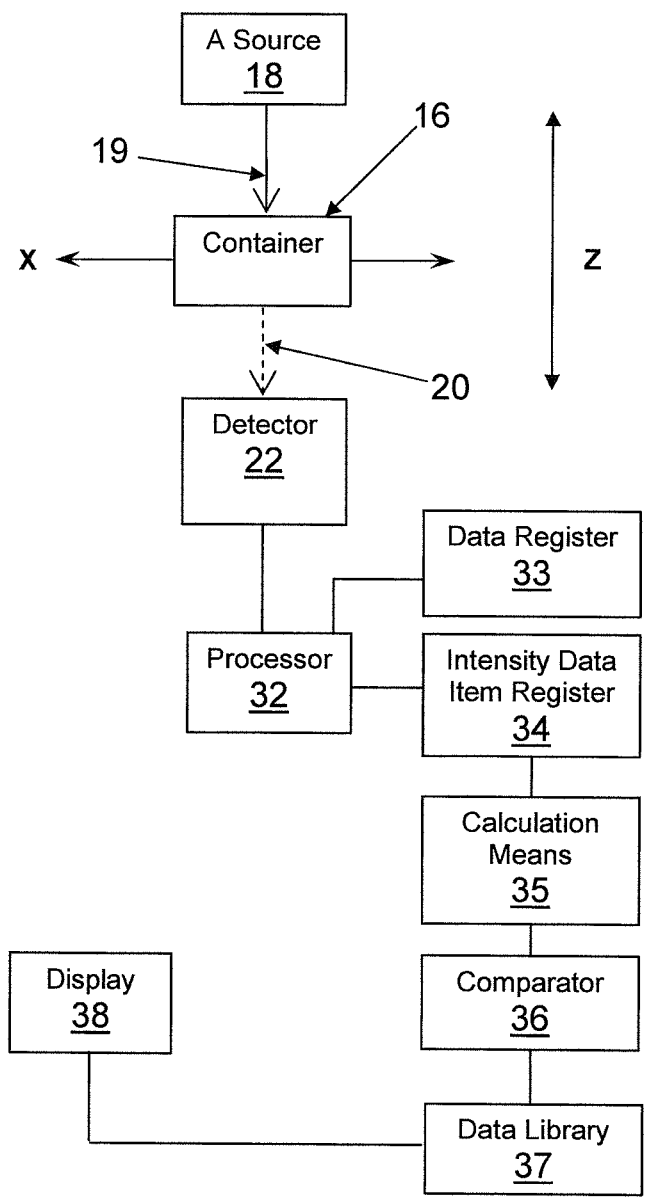
FIG. 2 is general schematic of a possible apparatus to implement the invention including an apparatus of FIG. 1.

In the general schematic representation of FIG. 2, a single ray path only is shown for simplicity. An x-ray source 18 and laterally spaced detector apparatus assembly 22 together define a scanning zone Z between them. In use, a bottle or other object to be scanned 16 is brought into an x-ray beam path by being placed in a holder such as the bottle holder shown in FIG. 1 and being moved in direction X through the scanning zone by a mechanism such as that described in FIG. 1 such that the x-ray beam passes through the bottle 16 along its axis.

In the illustrated example, a bottle 16 sits in the scanning zone Z. An incident beam 19 from the x-ray source is illustrated. In this simple schematic, the incident beam is represented by the line 19. The transmitted beam 20 is incident upon a single detector 22.

The detector 22 is in data communication with a processor 32. The inherent spectral resolution of the material in the detector allows the processor 32 to resolve this image differentially across a plurality of pre-set frequency/energy bands in accordance with the principles of the invention by reference to energy band boundaries stored in the data register 33.

In the example embodiment a tungsten x-ray source, is used. A typical spectrum such as might be generated by tungsten of initial intensity against wavelength is illustrated in FIG. 3.

Figure 3:
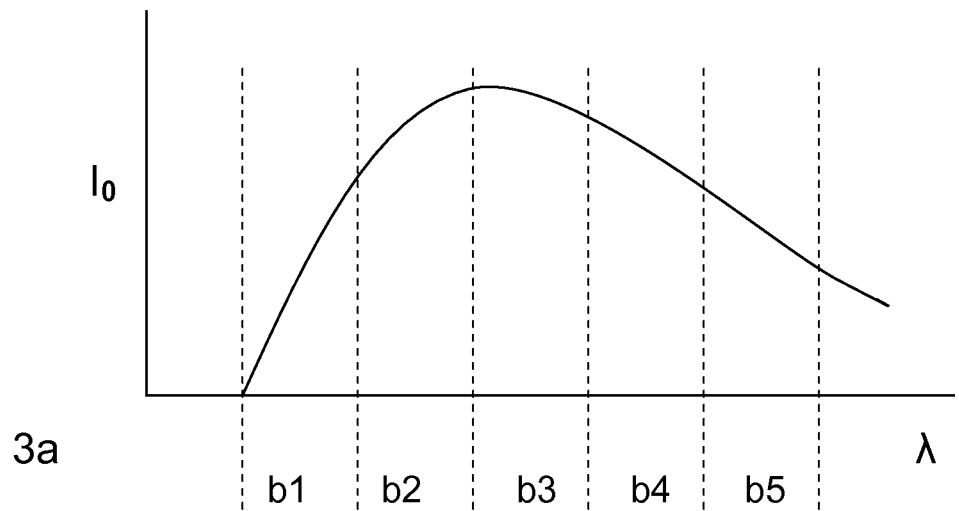
FIG. 3 illustrates a typical radiation source spectrum, and illustrates how it is partitioned to implement the invention in conjunction with an imaging operation.
Figure 3:
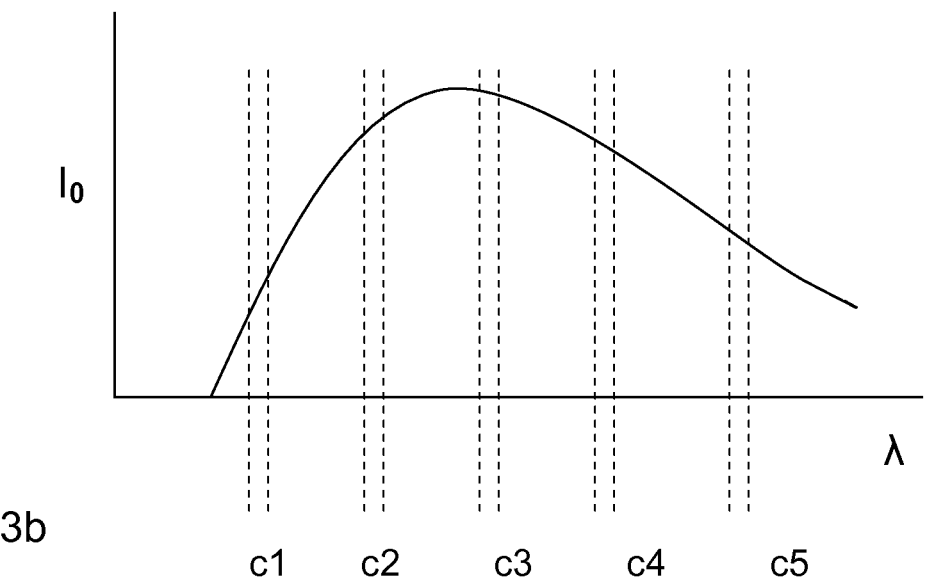

The main purpose of FIG. 3 is to illustrate two possible ways in which the spectrum may be resolved in accordance with a possible embodiment. In each case, the spectrum is shown resolved across five frequency bands.

The schematic illustrates two ways in which the spectrum may be resolved. In FIG. 3a, the bulk of the generated spectrum is divided between five relatively broad energy bands b1 to b5. In FIG. 3b, five relatively narrow bands, which may approximate even to individual energies, are defined c1 to c5. Neither alternative is in contradiction with the principles of the invention, and any combination may be used to generate useful results either for the numerical analysis of the invention or, in a preferred embodiment, for spectroscopically resolved imaging to give further information about an object and contents under investigation.

In the example embodiment, the data is used to characterise and identify the material contents of the bottle 16 under investigation. In the example embodiment, the data is analysed numerically. The processor 32 further acts in relation to a series of identified frequency bands, for example those in FIG. 3a or 3b, and in this function uses the data to generate a representative quantification of, and for example an average of, transmitted intensity in each band, which is then passed to the intensity data item register 34 for storage.

A calculation means 35 evaluates the data at points along the line scan of the bottle and attempts to fit it to a relationship in accordance with the method of the invention. For example, in a possible methodology, a first moving scan is performed where an $I_0$ value is taken as constant during the scan and anomalies are identified by anomalous trend data in transmitted intensity I. The method thus requires an $I_0$ reference dataset for the source across the spectrum under test which is conveniently generated in a calibration step before scanning by operating the system without an object.

The moving scan is used to identify anomalies indicative of suspicious structures or in homogeneities of content by this simple analysis of trend data. It may optionally be used to identify target sites for a second, static scan on which a more comprehensive analysis is performed with a view to materials identification.

In performing the second, static scan the object is moved to a fixed position by the scanning system. The motor is then switched off to prevent any electromagnetic interference and the radiation beam is passed through the object and contents to the detector where it is analysed without the interference from the motor to give a more accurate materials identification during a static scan cycle. The detector signal is analysed to derive a numerical material characteristic such as a coefficient of mass attenuation as a function of radiation energy and compared against a library of materials data to accurately identify the material or combination of materials present and/or to rule out the presence of any particular material.

For example at least attenuation at each band ($I/I_0$) is calculated In a possible further approach, the calculation means also evaluates a ratio between successive intensity data items (for example, where data items are collected I1 to I5 relating to energy bands c1 to c5, the calculation means evaluates the quotient I1/I2, I2/I3, I3/I4, I4/I5). This calculation of such a quotient is capable in principle of removing from consideration variables, such as density and thickness, which do not vary with incident radiation energy, and therefore of providing a numerical indicator which is functionally related to energy, and consequently indicative of the primary energy-dependent variable, the mass attenuation coefficient, by fitting to a relationship as above described.

An example of a relationship from which a suitable material coefficient can be derived is the exponential attenuation law for the transmission of x-rays through a material, as follows:

$$I/Io = \exp[-(82/\rho)\rho t] \quad (1)$$

μ/ρ=Mass attenuation coefficient. A material constant which is characteristic of the weighted elemental composition of a material
I=Final intensity
Io=Initial intensity
ρ=density of the material
t=thickness of the material This may be used to produce appropriate data representing the material under test in known manner, for example as described in Applicant's prior publication WO2009/024818.

Thus, for example, intensity data measurements resolved across a plurality of energy bands are analysed via the Beer-Lambert law set out in the equation above to derive the mass attenuation coefficient necessary to produce such an intensity pattern.

A comparator 36 compares the data thereby produced through the depth of the bottle with a library of data 37. The library of data may include pre-stored data of similar or at least numerically comparable nature which is related to or depends upon the mass attenuation constant for a range of materials, and in particular specified target materials. This may be a manually or automatically addressed library. Data may be preloaded or referenced, or may be generated or added to over time by operation of the apparatus with known materials. In the example case, library of data may include pre-stored analytical data for mass attenuation coefficients of a range of known materials, for example threat or contraband materials whose presence it is desirable to screen for.

By virtue of this comparison, inferences may be drawn about the likely material content in the transmission path. For example, the presence of a range of predetermined materials, for example threat or contraband materials, may be screened for by an elimination process to generate a result. This may be displayed on the display means 38 or the display can preferably be delayed until the scan cycle is completed as described below.

To carry out a bottle scan test to analyse the bottle contents a bottle to be investigated is loaded into the bottle holder and the test cycle started. The motor control, through the pulley and linear slide shaft assembly, moves the bottle to a position where it can start to be scanned. The x-ray beam is started and a measurement of the incident beam $I_0$ is made, after which the bottle is moved down so that the beam passes as a line scan down the axis of the bottle at the required position, for example at a position that maximises the thickness of the contents through which the x-ray beam passes.

The transmission beam detected generates an electrical signal that is analysed for intensity across the spectrum of beam energies to identify the material contents of the bottle in accordance with the method outlined in FIG. 2.

Due to noise from the stepper motor distorting the detector signal the first line scan with the motor running can only be used to verify compositional consistency through the depth of the bottle. In order to achieve the necessary throughput rate for the equipment in service only a limited number of counts (approximately 100) can be collected by the detector for each point along the line scan limiting the materials identification accuracy that can be achieved although an approximate identification of the bottle contents could be possible if the scan rate was slowed down to allow the detector to capture more counts or if higher counts rates could be achieved. To accurately identify the bottle contents the motor controller manoeuvres the bottle to a position where the beam will pass through a point selected by the comparator and a static scan of this point, or a number of points is carried out. A further measurement of $I_0$ is preferably made before the static scan in order to optimise the accuracy of $I/I_0$ calculations used to identify the material contents of the bottle.

The approximate analysis of the bottle content during the first line scan can identify the class of materials comprising the contents. As some materials are more easily characterised by the use of absorbers and filters to condition the beam any preferred beam conditioning absorbers and/or filters that might facilitate material identification can be selected and entered into the beam path before the second detailed static scan is carried out with the motor switched off.

The static scan can be carried out at one selected point or, alternatively, a series of points for the static scan can be selected and a series of data records taken and analysed to identify or verify the material identity.

A series of static scans can be carried out if, for example, the contents of the bottle appear to have a layered composition or there appears to be a plurality of regions with different compositions.

The static scan position or positions can be determined by an automated system in association with the comparator or determined by an operator monitoring the test.

One position for the static scan might be selected in the neck of the bottle above the liquid level to get a background absorption of the x-ray beam for the material of the bottle.

The invention claimed is:

1. A method of scanning objects expected to have relatively homogenous structure or contents to gain information about material content comprises the steps of:
   a) providing a radiation source and a radiation detector system spaced therefrom to define a scanning zone therebetween;
   b) in a first scanning step:
      i) causing an object to move relative to the source and detector system and collecting intensity information about radiation incident at the detector system after interaction with the object as it passes through the scanning zone;
      ii) monitoring of variation of incident intensity as the object moves through the scanning zone; and
      iii) using such variation of intensity to identify anomalous structures and/ or absence of homogeneity in the object and/or the contents thereof;
      iv) classifying an object returning such a result as suspicious; and
   c) in a second, subsequent scanning step:
      i) locating the object in a fixed position in the scanning zone and collecting intensity information about radiation incident at the detector system after interaction with the object as it is retained in the fixed position in the scanning zone;
      ii) resolving detected intensity information at a plurality of differentiated energy bands across at least part of the spectrum of the source;
      iii) analysing the incident intensity information against a suitable functional relationship relating transmitted to incident intensity;
      iv) comparing the results of that analysis with a library of suitable data to provide an indication of material content, which library comprises a database of undesirable, threat or contraband materials that it is intended to screen for;

v) returning a match to any item in the database as a result indicating presence of the material; and vi) classifying an object returning such a result as suspicious.

2. A method in accordance with claim 1 wherein the identification during the first scanning step comprises monitoring of variation of attenuation of incident intensity within predetermined tolerance limits as the object moves through the scanning zone and identification of anomalous structures and/or absence of homogeneity if the variation exceeds such predetermined tolerance limits.

3. A method in accordance with claim 2 wherein the identification during the first scanning step comprises:

a) the determination of discontinuities in the variation of attenuation of incident intensity that do not correspond to thickness/path length variation attributable to object shape, b) the interpretation of such discontinuities as a result indicating conformational anomaly and/or lack of homogeneity in the object and/or the contents thereof.

4. A method in accordance with claim 1 wherein collected intensity data comprising at least the intensity information collected during the second scanning step is numerically analysed against a suitable functional relationship relating transmitted to incident intensity and the results compared with a library of suitable data to provide an indication of material content.

5. A method in accordance with claim 4 wherein intensity information collected during the first scanning step is also analysed against a suitable functional relationship relating transmitted to incident intensity and the results compared with a library of suitable data to provide an initial indication of material content.

6. A method in accordance with claim 4 wherein a ratio is determined of incident to collected intensity, and this ratio is fitted to a suitable analytical relationship for a transmitted intensity attenuation mechanism, to determine a characteristic material data coefficient associated with the intensity attenuation mechanism.

7. A method in accordance with claim 6 wherein the ratio is used to determine a coefficient of mass attenuation.

8. A method in accordance with claim 7 wherein the analytic relationship is an exponential attenuation law and the intensity attenuation mechanism is photoelectric absorption.

9. A method in accordance with claim 1 wherein the first scanning step comprises moving an object relative to the radiation beam from the source and the detector system so that the beam passes through the object and contents and traces a path along a cross section of the object for a first scan which is a linear scan of transmitted intensity.

10. A method in accordance with claim 1 wherein the second scanning step comprises placing the object at a selected position relative to the radiation beam from the source and the detector system so that the radiation beam passes through the object and contents for a second scan which is a point scan of transmitted intensity.

11. A method in accordance with claim 1 wherein a calibration step is performed in which the system is operated without an object in the scanning zone and intensity information about radiation incident at the detector system is used to generate an incident intensity dataset, and this incident intensity dataset is used as a reference dataset to determine attenuation of the transmitted intensity during the first and/or second scanning step.

12. A method in accordance with claim 1 wherein the object is a container of contained material and the contained material has a single generally homogeneous composition.

13. A method in accordance with claim 12 wherein the container is mounted in a holder at an angle of between about 1° and about 80° from vertical.

14. A method in accordance with claim 13 wherein the container is mounted in a holder at an angle of between about 5° and about 30° from vertical.

15. A method in accordance with claim 1 wherein the radiation beam is arranged to pass through the object at an angle other than perpendicular to a surface thereof.

16. A method in accordance with claim 15 wherein the radiation beam is arranged to pass through the object at an angle of between about 5° and about 30° from normal to a surface thereof.

17. A method in accordance with claim 1 wherein the radiation source comprises a source to deliver high-energy ionising radiation.

18. A method in accordance with claim 1 wherein the source beam is collimated to produce a pencil beam.

19. A method in accordance with claim 1 wherein the radiation beam is collimated after interaction with the object under test to allow transmitted radiation to pass to the detector but to restrict any scatter radiation from reaching the detector.

20. A method in accordance with claim 1 wherein at least in relation to the second scanning step (c), the method comprises the further step of resolving intensity information to be detected at a plurality of differentiated energy bands across at least part of the spectrum of the source.

21. A method in accordance with claim 1 wherein the detector system exhibits a spectroscopically variable response across at least a part of the source spectrum and the method comprises retrieving intensity information spectroscopically resolved at a plurality of differentiated energy bands across the spectrum of the source.

22. A method in accordance with claim 21 wherein the detector comprises a detector element fabricated from a semiconductor material or materials selected to exhibit inherently as a direct material property a direct variable photoelectric response to source radiation.

23. A method in accordance with claim 22 wherein the detector comprises a semiconductor material or materials formed as bulk crystal including a Group II-VI semiconductor material.

24. A method in accordance with claim 22 wherein the detector comprises a semiconductor material selected from cadmium telluride, cadmium zinc telluride (CZT), cadmium manganese telluride (CMT) and alloys thereof.

25. A method in accordance with claim 1 wherein energy-selective absorbers and/or filters are introduced into the incident beam path prior to performance of the second, scanning step.

26. A method in accordance with claim 1 wherein intensity information collected at the detector is further used to generate an image of an object and contents in the scanning zone.

27. A method in accordance with claim 25 wherein information collected at the detector is resolved spectroscopically across a plurality of bands within the spectrum of the source and these are allocated to generate a series or composite of energy-differentiated images.

28. A method in accordance with claim 26 comprising the additional step of displaying a generated image.

29. A method in accordance with claim 1 wherein in the event that an object is classified as suspicious at step (b)(iv) or (c)(vi) the object is rejected from the scanning process and passed for further investigation.

* * * * *